(12) United States Patent
Lejkowski et al.

(10) Patent No.: US 11,697,102 B2
(45) Date of Patent: Jul. 11, 2023

(54) METHOD AND APPARATUS FOR ASSISTANCE OF THE PRODUCTION OF A FUNCTIONAL MATERIAL

(71) Applicant: HTE GmbH The High Throughput Experimentation Company, Heidelberg (DE)

(72) Inventors: Michael Ludwig Lejkowski, Ludwigshafen (DE); Michael Kraemer, Ludwigshafen (DE); Tilman Sauer, Heidelberg (DE); Andreas Strasser, Ludwigshafen (DE); Benjamin Rupp, Heidelberg (DE)

(73) Assignee: BASF SE, Heidelberg (DE)

( * ) Notice: Subject to any disclaimer, the term of this patent is extended or adjusted under 35 U.S.C. 154(b) by 0 days.

(21) Appl. No.: 17/641,957

(22) PCT Filed: Sep. 11, 2020

(86) PCT No.: PCT/EP2020/075496
§ 371 (c)(1),
(2) Date: Mar. 10, 2022

(87) PCT Pub. No.: WO2021/048372
PCT Pub. Date: Mar. 18, 2021

(65) Prior Publication Data
US 2022/0305452 A1   Sep. 29, 2022

(30) Foreign Application Priority Data

Sep. 13, 2019 (EP) ...................................... 19197347

(51) Int. Cl.
*B01J 19/00* (2006.01)
(52) U.S. Cl.
CPC ......... *B01J 19/004* (2013.01); *B01J 19/0033* (2013.01); *B01J 19/0053* (2013.01)
(58) Field of Classification Search
CPC ... B01J 19/004; B01J 19/0033; B01J 19/0053
See application file for complete search history.

(56) References Cited

U.S. PATENT DOCUMENTS

2002/0086791 A1   7/2002   Iglesia et al.

FOREIGN PATENT DOCUMENTS

| FR | 2865819 A1 | 8/2005 |
| WO | 2013175240 A1 | 11/2013 |
| WO | 2018035718 A1 | 3/2018 |

OTHER PUBLICATIONS

Andreas Sundermann et al: "High-Throughput Screening as a Supplemental Tool for the Development of Advanced Emission Control Catalysts: Methodological Approaches and Data Processing", Catalysts, Bd. 6, Nr 2, Feb. 1, 2016.

(Continued)

*Primary Examiner* — Lessanework Seifu
(74) *Attorney, Agent, or Firm* — Lowenstein Sandler LLP

(57) ABSTRACT

A method and apparatus for monitoring and evaluation of a production of a functional material, wherein an assessment of steps taken by users based on a data basis results in reporting to the user of the extent to which predetermined properties of a functional material produced are attained in the event of variances in the steps taken.

15 Claims, 5 Drawing Sheets

(56) References Cited

OTHER PUBLICATIONS

Lutze P et al: "Process intensification: A perspective on process synthesis", Chemical Engineering and Processing, Elsevier Sequoia, Lausanne, CH, Bd. 49, Nr. 6, Jun. 1, 2010 (Jun. 1, 2010), Seiten 547-558.
European Extended Search Reported for Application No. 19197347.8 dated Mar. 2, 2022, 8 pages.
International Search Report and Written Opinion with English translation for PC/EP2020/075496 dated Oct. 21, 2020, 16 pages.

METHOD AND APPARATUS FOR ASSISTANCE OF THE PRODUCTION OF A FUNCTIONAL MATERIAL

CROSS REFERENCE TO RELATION APPLICATION(S)

The present application is a national stage entry under 35 U.S.C. § 371 of International Application No. PCT/EP2020/075496 filed on Sep. 11, 2020, which claims priority to European Application No. 19197347.8 filed on Sep. 13, 2019, the contents of which are incorporated by reference in their entirety.

FIELD OF THE INVENTION

The present invention relates to a method and an apparatus that permits users to have a functional material such as a catalyst designed, and especially permits guiding through the execution and recording of all necessary parameters.

BACKGROUND OF THE INVENTION

The activity of a catalyst depends significantly on its production history. The selection of the ingredients, various parameters of various process steps that lead to the post catalyst, and the chemical composition of the finished catalyst can have a considerable influence on catalyst activity.

It is therefore very important to record and to store the abovementioned information in a relational database in a structured and hierarchical manner. This forms the basis for later recognition of structure-activity relationships.

US 2002/0086791 A1 discloses a machine approach that provides a projection for development of scalable heterogeneous catalysts and solids having high-performance properties. This machine approach comprises three main components: the data generation cycle by means of high throughput methods, the knowledge generation cycle, and the recording of knowledge or database.

WO 2013/175240 discloses a method of producing a product that is said to meet or surpass the properties expected by the user, wherein an algorithm is used to optimize the method. The method described in WO 2013/175240 is a flow system, with the analysis system adapted to the flow system.

A. Sundermann et al., "High-throughput screening as a supplemental tool for the development of advanced emission control catalysts: Methodological approaches and data processing", vol. 6, no. 2, p. 23, February 2016, for example, discloses a high throughput screening method for the development of advanced catalysts for emission control.

D. Lutze et al., "Process intensification: A perspective on process synthesis"; Chemical engineering and processing, Elsevier Sequoia, vol. 49; no. 6, pp. 547-558, June 2010; discloses process intensification for a process synthesis.

WO 2018/035718 A1 discloses a prediction model that is said to enable true real-time prediction of the production rates of chemical products in chemical plants.

SUMMARY OF THE INVENTION

The present invention relates to a method and apparatus for monitoring and evaluation of a production of a functional material according to the independent claims; further embodiments of the invention are embodied in the pending claims.

In one embodiment of the invention, a method of monitoring and evaluating a production of a functional material is provided, wherein the method comprises: providing a multitude of defined processes to a user, each with defined process parameters of a process for the production of a functional material and properties thereof; recording steps taken by the user in implementing a process selected from the multitude of processes; comparing the steps taken by the user with the process parameters of the selected process for the production of a functional material, assessing the steps taken by the user based on a data basis having a multitude of processes implemented by earlier users with process parameters for the production of functional materials and the analyzed properties thereof; reporting to the user the extent to which predetermined properties of the functional material produced by the implemented process are attained in the event of variances of the aforementioned steps in an implementation of the process selected from the defined process parameters of the selected process.

In this way, a knowledge basis can be made available to a user in the production of functional materials, which assists the user in researching functional materials, controlling the parameters thereof and predicting the results, in order in this way to enable a more efficient procedure in the systematic researching and production of functional materials.

The expression "materials" or "functional materials" is nonlimiting and encompasses all materials, including input and output materials, that are used in conjunction with the performance of the process. In the context of the present description, the input materials are also referred to as precursor materials, which can in turn be produced from the pre-precursor materials, such that the corresponding process parameters that describe the different material relationships (the production history) and the properties can be stored in the method. In principle, in a process, it is possible to consider the chemical composition, and also the process step parameters (for example the calcination temperature in the calcination) to which chemical compositions can be subjected. Input and output materials can ultimately be described by proportions by mass of (alias) components. A composition in relation to the chemical elements can be described by different relationships in the form of formulae. Individual properties can then be described in the form of a physical parameter. In the context of the invention, however, process parameters shall be understood to mean both material parameters, e.g. chemical compositions in relation to the chemical elements, or substances or materials, and process parameters.

The data basis may include comparative data and/or reference data. The data basis has, as comparative data and/or reference data, for example, a multitude of processes implemented by earlier users with process parameters for the production of functional materials and the analyzed properties thereof. Comparative data and/or reference data may also be analytically generated data, or else correlations between process parameters and properties that have been taken from the literature or earlier analyses.

The parameters that characterize a material may be physical and chemical parameters, with the individual ingredients counting among the chemical parameters that are reported via the type and amount of the elements present in the materials and being determined, for example, in an elemental analysis of the material. In addition, a material may be characterized by one or more parameters selected from the group of identification number or registration number, date of production, name of manufacturer, container identification number and/or material ID. A multitude of parameters is available for description of materials.

Earlier users are understood in this context to mean an assignment to a process conducted in the past, regardless of the identity of the user. More particularly, the earlier user may be the same person as the current user. The process being undertaken by the current user can also be sent to the data basis, such that the process implemented by the current user becomes a process implemented by an earlier user.

The assessment may also comprise the registering of the properties and the registering of variances in order in this way to give the user an indication as to whether the process is likely to lead to the desired success.

A functional material may be any material having a physical, biological and/or chemical functionality. By way of example, but in a non-exclusive manner, these may be inorganic functional materials, for example but not exclusively solid-state catalysts, battery materials or adsorbents. Inorganic functional materials may be provided with appropriate performance properties; for example, solid-state catalysts may be specified according to their selectivity, activity and/or service life in the process under given process conditions, adsorbents according to their adsorption capacity, according to substance-specific properties and/or service life, and battery materials according to their energy density, lifetime and/or safety.

Impermissible variances in relation to parameters exist when defined parameters are exceeded, with the value of the exceedance being greater than the value of the error tolerance. Impermissible variances in relation to materials exist when there is incorrect assignment, which can be recognized with reference to an identifier. Impermissible variances may be registered. At the same time, intervention by the user may be undertaken in order to eliminate impermissible variances.

Compared to the known prior art, for instance A. Sundermann et al., "High-throughput screening as a supplemental tool for the development of advanced emission control catalysts: Methodological approaches and data processing", the invention enables not just testing of functional materials but also the monitoring of the production. Furthermore, the invention; with respect to the prior art; enables comparison of the steps taken by the user with the process parameters of the selected process for the production of a functional material. This enables making of the assessment of the steps taken by the user based on a database having a multitude of steps taken by earlier users based on a data basis having a multitude of processes implemented by earlier users with process parameters for the production of functional materials and the analyzed properties thereof. As a result, in the event of a variance of process parameters of the selected process for producing a functional material, the resulting influence on the properties of the functional material can be predicted and communicated to the user. For instance, the user is informed when a variance of process parameters in the method chosen leads to a change in the properties of the functional material produced. Especially when the properties of the functional material produced deteriorate on account of the variance from the process parameters of the chosen process, the user is warned and can intervene in the process to be executed. This enables efficient procedure in the systematic search for and production of functional materials.

In one embodiment of the invention, the providing of defined processes may also include the possibility of modifying existing processes and/or adding on processes.

In this way, a higher flexibility of the method is achieved, and easier modification of the procedure is enabled.

In one embodiment of the invention, the providing of defined processes may also include the possibility of creating workflow instances.

In this way, it is possible to subject similar samples having particular variations of individual parameters of a workflow to the method. These may be illustrative procedures in which variations are permitted. The variation of individual parameters may be helpful in order to analyze particular effects and can make a contribution to optimization of functional materials.

In one embodiment of the invention, the method further encompasses assistance for a user in a projection calculation, wherein the assistance especially comprises calculating relationships and/or recalculating parameters, wherein, in particular, at least some of the processes are scalable and a user is given the choice of dimensions of these processes. In one embodiment, in a projection calculation, it is possible to create what is called a multiple ratio table, and to provide grouping of elements, (alias) components and materials. It is possible here to use groups as reference in the relational tables as well.

In this way, the user is given extensive assistance in the production of a functional material in that the process steps conducted are not just recorded or registered and subjected to the assessment, but the user is also given assistance before and in the course of performance of the steps that avoids errors.

In giving assistance, the method may also provide supplementary information or else search functions, and assisted or automated alias name assignment. In giving assistance, it is also possible, for example, to provide information describing the stoichiometric components and alias components, including proportions by mass. A search function may also include searching for samples according to their production history (method parameters) or ingredients (material parameters, e.g. Fe, Co, Ni, . . . ). A search function may also enable searching of the data basis for selected parameters, process parameters, parameters in the composition, for example a search for samples with a platinum active component in the range of 0.05-1% by weight, or research the samples that have been produced with a material of a specific support oxide.

In one embodiment of the invention, the method also offers the giving of what are called alias names for placeholders in general or else as placeholders for parameters.

In this way, assisted assignment is possible, which also enables the discovery of a material under its trivial name. In principle, materials may be described by multiple components. A component may have a chemical formula, for example NaCl for sodium chloride. An alias component is a variant of the component that simply has only a name/label, but need not have, for example, any information as to its chemical composition. Components may be used later on in relationships for the projection calculation. If components are described by a formula, the relationships may also include the chemical elements present.

In one embodiment of the invention, the method further comprises monitoring of a user in implementing the steps made in a process selected from the multitude of processes.

In this way, it is possible to ascertain at an early stage whether the user is undertaking an incorrect operation or is not working according to the process, or is working outside predetermined rules.

In one embodiment of the invention, the monitoring comprises comparing at least one step intended by the user with an appropriate process parameter of a selected process for the production of a catalyst, and a warning in the event of an impermissible variance.

In this way, it is possible to give a direct response to the user in the event of a variance, or else to other people or monitoring devices that can then optionally intervene in the process to be implemented.

In one embodiment of the invention, the monitoring comprises reading of an identifier of a reservoir vessel of a material provided by a user and a comparison with a material provided for the corresponding defined process, and a warning in the event of an impermissible variance.

In this way, it is also possible to monitor the selection of material by the user in an automated manner, especially in order to compensate for human mistakes, such as misreading or not looking properly. This can also assist a robot-assisted mode of operation.

In one embodiment of the invention, for identification, the individual materials can be assigned an identification number or a registration number. It should be noted that each individual sample is assigned a dedicated identification number, such that, for example, a pulverulent support oxide receives a different ID number than that sample which is taken as a portion for further processing from the overall sample. Thus, every material and all samples associated with the material can be stored in the data basis in a discoverable manner.

In one embodiment of the invention, a process parameter or a step taken by the user comprises at least one material parameter or one processing parameter, and/or an origin parameter of a material.

In this way, it is possible to define the process steps, by material selection or process step selection, such as temperature or treatment time, and to select them.

In one embodiment of the invention, the assessing of the steps taken by the user comprises employing of artificial intelligence which, on the basis of the multitude of processes executed by earlier users stored in the data basis for the production of catalysts and the measured properties thereof, establishes a correlation of at least one process parameter of a process for the production of a catalyst and at least one property of the catalyst.

In this way, it is possible to achieve an additional information gain that goes beyond pure combinatorics. Any further process sent to the data basis can enable identification of further correlations, such that it is possible to predict with greater accuracy what effects particular parameters have and what effects particular variances of these parameters can have. In this way, it is possible to reduce the number of experiments required to produce a particular functional material with the desired properties.

In one embodiment of the invention, on the basis of the correlation and the steps taken by the user in an implementation of the selected process, a prediction is created for at least one property of the catalyst to be produced.

In this way, it is possible to create a specific prediction as to which properties a functional material is likely to have when it is produced by a process to be executed.

In one embodiment of the invention, the assessing of the steps taken by the user comprises an intermediate assessment on the basis of an intermediate result based on a data basis comprising a multitude of processes implemented by earlier users for the production of precursor materials and the measured properties thereof.

In this way, even in the case of intermediate stages, it is possible to evaluate whether these have certain desirable properties and whether it is foreseeable whether the final material will also display the desired properties. In this way, it is also possible on the other hand to terminate a process at an early stage if it can already be seen from the precursor material that the final material will not gain the desired properties.

Precursor material refers to a material which is used as basis for production of a functional material. Precursor materials can occur in various generations of a multistage process. Precursor materials may already have properties also possessed by the ultimate functional material. For example, a pulverulent catalyst which is converted to a shaped catalyst body by means of extrusion may be a precursor material.

In one embodiment of the invention, a method is provided for establishing a data basis for employment of a method of monitoring and evaluating a production of a functional material, wherein the method of establishing a data basis comprises: recording steps taken by users in an implementation of a process for production of a functional material; analyzing properties of the functional material produced by the process for producing a functional material; assigning the properties of the functional material produced by the process for producing a functional material to the corresponding steps in an implementation of the process for producing a functional material; and storing the result of the assignment in the data basis.

In this way, it is possible to establish a data basis that serves as a knowledge basis in the production of functional materials. Data from previous processes are collected, such that a correlation between the process parameters such as materials and process parameters and the properties of the finished material can be established. This correlation can then also be applied to the current process in the production of a functional material.

In one embodiment of the invention, the method of establishing a data basis comprises employing of artificial intelligence which, on the basis of the multitude of recordings of steps taken by users in an implementation of a process for producing a functional material and the analyzed properties thereof, establishes a correlation of at least one process parameter of a process for the production of a functional material and at least one property of the analyzed functional material.

For example, it is possible to establish and use a neural network in order to increase the "knowledge content" of the data basis. This leads to significantly higher efficiency in the production of the functional material.

In one embodiment of the invention, the method of the invention performs the assessment of the steps taken by the user using artificial intelligence.

In general, for the term "artificial intelligence", a distinction is drawn between strong artificial intelligence and weak artificial intelligence. Strong artificial intelligence attempts to simulate man as a person. The term "weak artificial intelligence" relates to means of independent learning processes, optimization by employment of defined algorithms for neural networks, especially also recognition of patterns.

In one embodiment of the invention, an apparatus is provided for monitoring and evaluating a production of a functional material, wherein the apparatus comprises: a user interface; a processing unit; a catalog having a multitude of defined processes, each with defined process parameters of a process for the production of a functional material; and a data basis having a multitude of processes implemented by earlier users for the production of functional materials and the analyzed properties thereof; wherein the user interface is set up to provide the user with the catalog for selection, and to enable the user to select a process for the production of a functional material;

wherein the user interface is set up to record steps taken by the user in implementing a process selected from the multitude of processes; wherein the processing unit is set up to compare the steps taken by the user with the process parameters of a selected process for the production of a functional material and to assess the steps taken by the user based on the data basis with regard to properties expected to be achieved in the functional material; wherein the user interface is set up to report to the user the extent to which predetermined properties of the functional material produced by the implemented process are attained in the event of variances of the aforementioned steps in an implementation of the process selected from the defined process parameters of the selected process.

In this way, it is possible to provide an apparatus that assists the process of production of a functional material. The user can be assisted by the apparatus in that the apparatus provides the user with certain selections and restricts other selections that are not productive according to defined rules. More particularly, it is also possible to avoid avoidable errors in the calculation, dosage and selection of materials and process parameters.

In one embodiment of the invention, the apparatus comprises a monitoring device set up to compare at least one step intended by the user with an appropriate process parameter of a selected process for the production of a functional material, and to give a warning to the user in the event of an impermissible variance.

In this way, it is possible to give a direct response to the user in the event of a variance, or else to other people or monitoring devices that can then optionally intervene in the process to be implemented.

In one embodiment of the invention, the apparatus comprises a reading device for an identifier of a reservoir vessel of a material provided by a user, wherein the apparatus is set up to make a comparison with a material provided for the corresponding defined process, and to give a warning in the event of an impermissible variance.

In this way, it is also possible to monitor the selection of material by the user in an automated manner, especially in order to compensate for human mistakes, such as misreading or not looking properly. This can also assist a robot-assisted mode of operation.

In one embodiment of the invention, the monitoring device includes a reading device set up to read an identifier of a reservoir vessel of a material provided by a user, wherein the monitoring device is set up to compare the content of the identifier with a material provided for the corresponding defined process, and to give a warning to the user in the event of an impermissible variance.

In this way, it is possible to automatically record whether the correct material has been selected and, in the event of an incorrect selection, to give a warning message. Rather than an identifier, it is also possible to effect a direct analysis of the material to be supplied, and optionally to give a warning depending on the analysis result.

In one embodiment of the invention, the processing unit comprises artificial intelligence set up, on the basis of the multitude of processes executed by earlier users stored in the data basis for the production of functional materials and the measured properties thereof, establishes a correlation of at least one process parameter of a process for the production of a functional material and at least one property of the functional material.

For example, it is possible to establish and use a neural network in order to increase the "knowledge content" of the data basis. This leads to significantly higher efficiency in the production of the functional material.

In one embodiment of the invention, on the basis of the correlation and the steps taken by the user in an implementation of the selected process, a prediction is created for at least one property of the functional material to be produced.

In this way, the apparatus can significantly accelerate the production process, especially since a production process can be shortened if it is foreseeable that it will not lead to the desired success on the basis of the prediction.

These and other features are elucidated by the description of figures that follows.

Further features and advantages of the methods of the invention and of the apparatus are apparent from the figures and from the accompanying description of figures. It will be apparent that the features which have been mentioned above and those which are still to be elucidated below can be used not only in the combination specified in each case but also in other combinations or on their own without leaving the scope of the invention. Working examples of the invention are shown in the figures and are described in detail hereinafter.

DETAILED DESCRIPTION OF ILLUSTRATIVE EMBODIMENTS

Figure 1:
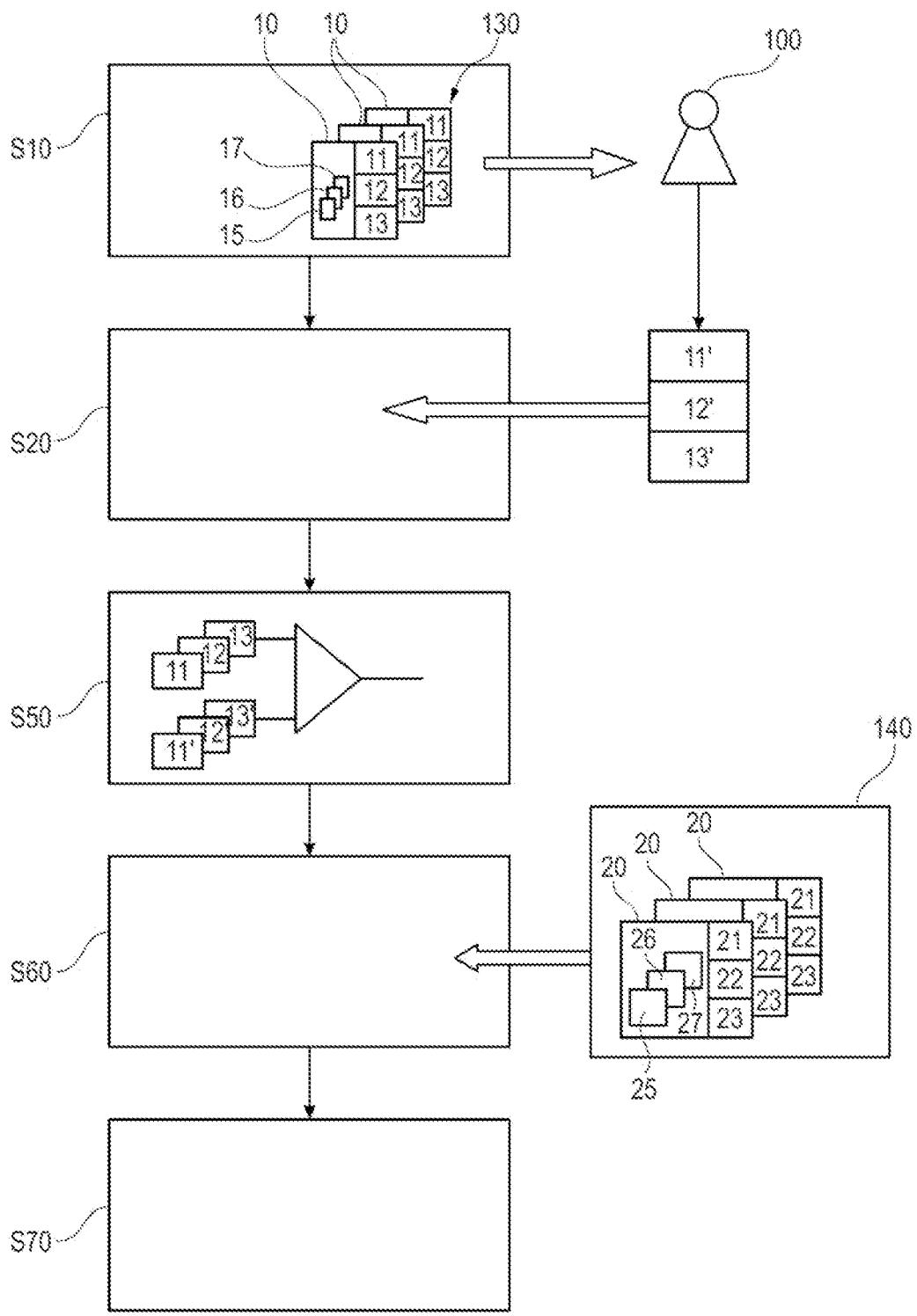
FIG. 1 shows a schematic sequence of a method of monitoring and evaluating a production of a functional material in one embodiment of the invention.

FIG. 1 shows a schematic sequence of the method of monitoring and evaluating a production of a functional material in one embodiment of the invention.

In step S10, a catalogue 130 with multiple processes 10 for production of a functional material, for example a catalyst, is provided. The processes are each defined by process parameters 11, 12, 13. Also recorded under the processes 10 are the properties 15, 16, 17 of the functional material produced by the respective process 10. The user 100 is able to select a process 10 that leads to the desired functional material from the processes provided. The selected process may also serve as a basis for modifying the selected process 10. The steps 11', 12', 13' taken by the user that correspond to the process parameters of the process actually implemented are then recorded in step S20. The steps 11', 12', 13' actually undertaken may vary from the process parameters 11, 12, 13 of the selected process 10, which then possibly leads to a different property of the functional material. This variance may be intended, for instance resulting from a controlled modification of the process 10, or unintended, for example resulting from a mistake in the implementation or from measurement inaccuracies in materials or process parameters. The steps 11', 12', 13' actually conducted are then compared with the intended steps or process parameters 11, 12, 13 in step S50. The result of the comparison is then used as a basis for comparing this in step S60 with a data basis 140 in which processes 20 are stored, i.e. process parameters 21, 22, 23 which have led to particular properties 25, 26, 27 in the production of functional materials. The data basis 140 may include a multitude of processes 20 that have been conducted by earlier users. On the basis of these processes 20, it is possible to infer whether the intended process 10 leads to the desired success or not. However, the data basis 140 may consist not only of real earlier processes 20, but may also contain correlations derived from processes, correlations between process parameters 21, 22, 23 and properties 25, 26, 27 based on an analytical determination, or else on the application of artificial intelligence. In step S70, a report is then made to the user as to whether the desired property is attained, to what extent it is attained, and/or what measures have to be taken in order to achieve the desired result.

Figure 2:
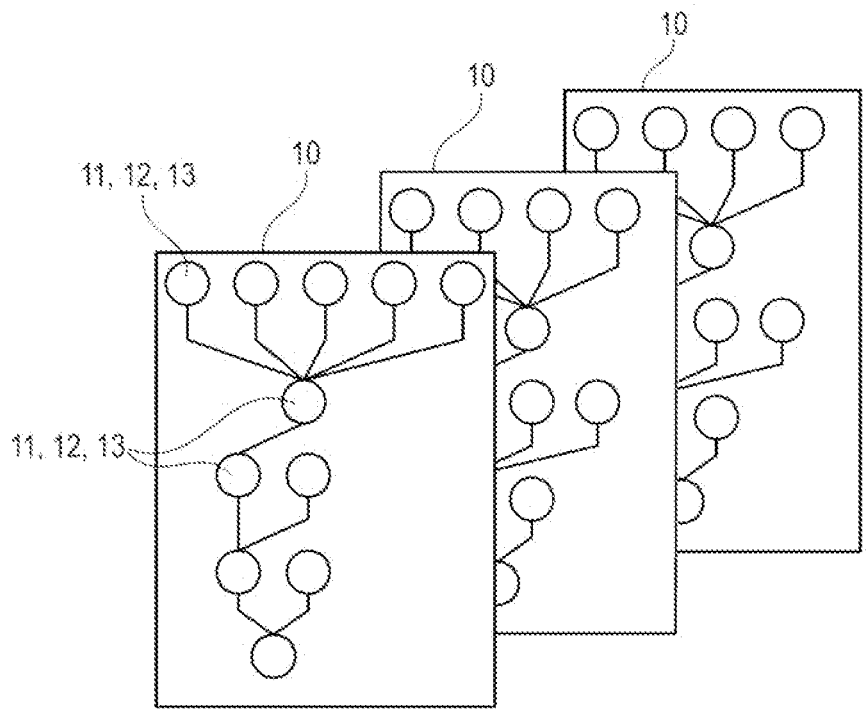
FIG. 2 shows a more detailed structure of the processes or of a process catalogue of the method shown in FIG. 1 in one embodiment of the invention.

FIG. 2 shows a more detailed structure of the processes of a process catalogue of the method shown in FIG. 1 in one embodiment of the invention. FIG. 2 shows that the process may have a branched tree structure. In an early level (upper row), it is possible to choose different starting points or process parameters 11, 12, 13, for instance different materials. These can then be presented to the user for selection in step S10. In the later levels, there may be branches which are selected according to selected process parameters in a later level (further down). These may be material selections or else processing selections, for instance the selection of a treatment temperature or a treatment time. These can then likewise be presented to the user for selection. The selection here may be restricted to particular parameters according to defined rules. For example, parameter selections 11, 12, 13 which, on the basis of the "knowledge" of the data basis 140, will not lead to a promising result 15, 16, 17 are withheld from the user by the method. Later on, further materials can be supplied to the process, according to what is recorded in the selected process 10.

Figure 3:
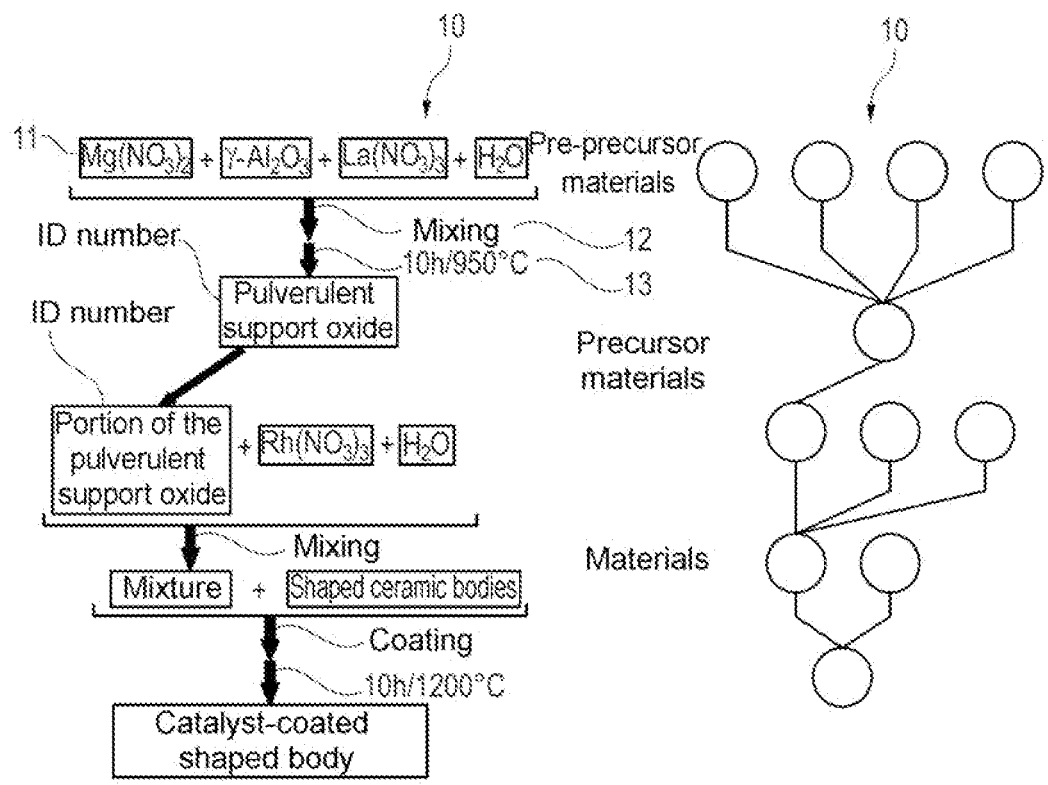
FIG. 3 shows a comparison of a process flow diagram from FIG. 2 with a process having process parameters in one embodiment of the invention.

FIG. 3 shows a comparison of a process flow diagram from FIG. 2 with a process 10 having process parameters 11, 12, 13 in one embodiment of the invention. FIG. 3 shows an illustrative process on the left, and the process depicted in a tree structure on the right. The vertical axis shows the progression in a production of materials, with individual process parameters, for example materials supplied and process steps, indicated by a circular symbol. In the upper region, starting materials that lead to production of a functional material are identified, which is indicated by the circle in the lower region. The intervening circles may represent precursor materials if these are used as input parameters for a further process step. By way of illustration of a process 10, FIG. 3 shows the schematic sequence of a multistage method of producing a coated rhodium catalyst on a ceramic shaped body. The example illustrates the relationships of the materials and the compounds thereof with precursor materials and pre-precursor materials. The example concerns the production of oxidation catalysts in which an aluminum oxide is used as aluminum source, which is first converted to a pulverulent mixed oxide. Thereafter, a portion of the pulverulent mixed oxide with active component (rhodium nitrate in the present case) is mixed with water, and the mixture is used to coat a shaped ceramic body. After the coating, the shaped body is subjected to a thermal treatment.

Figure 4:
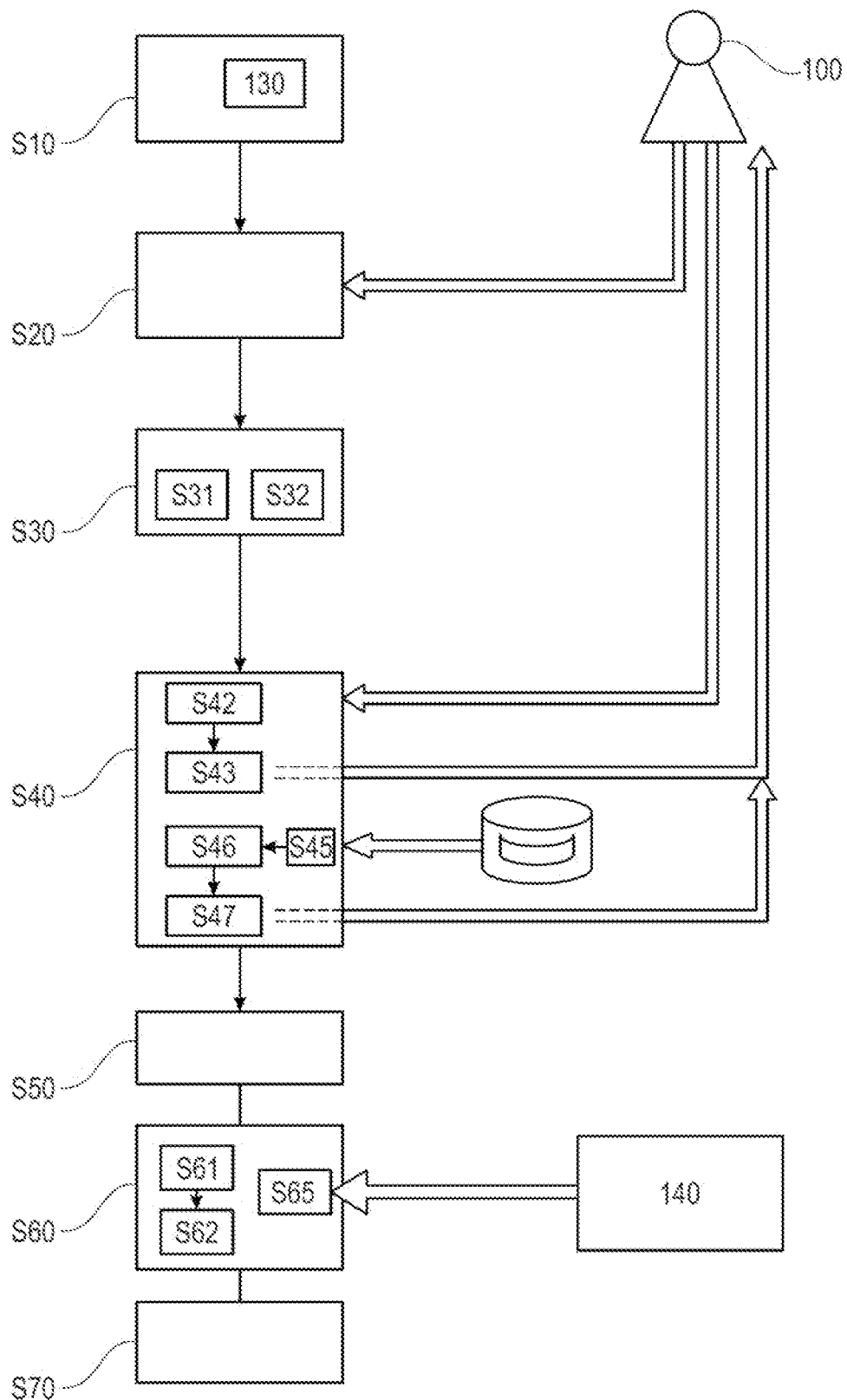
FIG. 4 shows a more detailed process sequence compared to the process sequence shown in FIG. 1 for monitoring and evaluating a production of a functional material in one embodiment of the invention.

FIG. 4 shows a more detailed process sequence compared to the process sequence shown in FIG. 1 for monitoring and evaluation of a functional material in one embodiment of the invention. The method may also comprise assistance S30 for a user 100 in a projection calculation, wherein the assistance especially comprises calculating S31 of relationships and/or recalculating S32 of parameters. In particular, at least some of the processes 10 are scalable and a user 100 is given the choice of dimensions of these processes 10. The user can be provided with numerous tools that make it easier to select and to judge the process parameters 11, 12, 13. In a projection calculation, it is possible to provide what are called multiple ratio tables and the grouping of elements, (alias) components and materials. Groups may be used as reference in the ratio tables as well. For example, the group of "precious metals" may consist of rhodium, platinum and palladium. For this purpose, it is then possible to state in a multiple ratio table that these elements are set in a molar ratio of 1:2:3. The group of "precious metals" can then be put in another ratio table with water and a carrier material in a weight-based relationship, for example: "precious metals": water:support=1:50:100. On this basis, it is impossible to calculate required amounts of the starting materials for a particular batch size.

Materials can be defined by import from the system inventory or by direct new entries in what is called a synthesis request, or described directly in terms of their chemical composition. A material may comprise multiple components that are described by chemical formulae, for example in that the molar mass of the material is calculated automatically and/or the proportions by mass per component are calculated automatically from the purity or the presence of impurities, especially the type and amount of impurities. This information is important for later projection calculations. Materials may also be described directly with components and proportions by mass. In addition, a description with alias components that do not have a chemical composition is possible, for example "impurity". It is possible to input further properties for materials that influence later projection calculations, for example concentration, density, loss on ignition (LOI) and/or solvent absorption.

A formulation editor may be provided, and is intended primarily for the scientist planning the production of samples. It offers two major functionalities: a projection calculation of ingredients for a preparation, and a description of the production method via preconfigured process steps with parameters. In the projection calculation, it is possible to choose between different modes of calculation. These modes offer further selection options that influence the projection calculation. In a second step, the input materials may be selected. All materials are available here from a material tab/menu, as are materials that are planned or have been produced in the current synthesis request. In order to calculate the projection calculation, it is also possible to make the following statements of amount: total amount of all input materials, total amount of the target product (optionally taking account of an expected yield), and/or amounts of individual input materials. Subsequently, further boundary conditions can be defined for the projection calculations, for example ratios of particular materials, components, alias components of chemical elements.

In a "chemical solution" calculation mode, an input material can be selected as solvent. In an "impregnation"

calculation mode, and input material can be selected as support and a further input material as solvent. The solvent absorption of the support influences the calculation of the amount of solvent required. The LOI (loss on ignition) of the support is taken into account for the defined loading of the support. The LOI is the ignition loss, which is ascertained, for example, in conjunction with the baking-out of a support. Based on the boundary conditions, the amount of the input materials required is calculated. If no calculation is possible owing to missing or contradictory inputs, the user is informed in the "Messages" tab/menu. The result of the calculation can be displayed. This comprises the necessary weights of the input materials that satisfy the boundary conditions entered.

The process steps may be configured in a separate administration step by users having particular rights. In addition to the parameters, it is also possible to offer auxiliary calculations. For example, a "monolith coating" method step may have the parameters "start weight", "wet weight" and "dry weight". The user is ultimately interested in the increase in weight after coating. In the administration view, it is possible to record formulae that can access the parameters of the method step, for example "dry gain after coating [g]"="dry weight" minus "start weight". These auxiliary calculations can be displayed as read-only values during the execution, as soon as the parameters needed for the calculation have received a value from the user. This helps the user to decide whether they still have to change the parameters further or not.

Process steps may have a name and describe a particular operation, for example filtration or calcination. A process step may have several parameters that are identified by a name, a value with a particular data type (series of characters, text block, integer, numerical value, equipment or material), and for numerical values by a unit. A piece of equipment may itself in turn have its own parameters, for example a speed for a rotary mixer. There is a separate administration view for the management of equipment. Particular parameters stipulate that a process step gives rise to a by-product. Examples of these are process steps such as sieving or centrifuging. A projection calculation and any sequence of process steps may be associated with one another in what is called a workflow. A workflow thus describes which input materials are required in which relations and which process steps are conducted in order to obtain the desired result sample. Workflows may include the following elements: name; projection calculation the calculation mode, selection of input materials and details of the ratios of the input materials or components thereof or chemical elements. In a graphics editor, it is possible to pull multiple process steps by drag & drop into an existing workflow. These are to be conducted in a chronological sequence later in the implementation. It is possible to input target values for the parameters for each process step. It is possible here to convert the unit in the case of numerical and integer values, for example from g to kg. Values already entered are then converted. In addition, comments can be entered for individual parameters or for the entire process step.

A new sample may result in a new material or be stored under an existing material. The name of a new material can be given via a formula comprising variables and text elements. In addition, new calculation properties and the composition of the result sample can be entered. In particular cases, this composition can be calculated automatically. If the total amounts of input materials required are worked out in a workflow, it is possible to divide them into portions for each material. This may be necessary when the addition of particular amounts in a time-dependent manner is desired. Weight ratios can be entered for the portions. The portions created can be selected in the process steps of the workflow as a parameter of the type of material, meaning that it is possible to state when which portion is to be utilized. A global calculation can be used to conduct a projection calculation without accompanying process steps, and without giving rise to a result sample. One calculation mode available here is physical mixing according to weight ratios. The calculation of divided portions is possible. For divided portions, it is also possible to state a target amount. This input scales the portion chosen without affecting the other portions. The amounts calculated per material can be used in later workflows, in which case the amount calculated is automatically adopted as well.

In addition, FIG. 4 shows that the method comprises monitoring S40 of the steps 11', 12', 13' taken by the user 100, in which at least one of the steps 12', 13' intended by the user is compared S42 with an appropriate process parameter 11, 12, 13 of a selected process 10. It is thus possible to monitor the production of a functional material, for example a catalyst, and to give a warning S43 in the event of an impermissible variance. This can be effected, for example, when the user has executed a wrong step and/or the result of a step would not lead to the desired result. For this purpose, it may also be envisaged that an identifier of a reservoir vessel containing a material envisaged by a user is read 45, and this is compared S46 with a material envisaged for the corresponding defined process. It is optionally possible to give a warning S47 in the event of an unexpected variance.

In addition, FIG. 4 shows that the assessing S60 of the steps taken by the user 100 comprises employing of artificial intelligence S65 which, on the basis of the multitude of processes 20 executed by earlier users stored in the data basis for the production of functional materials and the measured properties thereof 25, 26, 27, establishes a correlation of at least one process parameter 11, 12, 13 of a process 10 for the production of a functional material and at least one property of the functional material 25, 26, 27.

Figure 5:
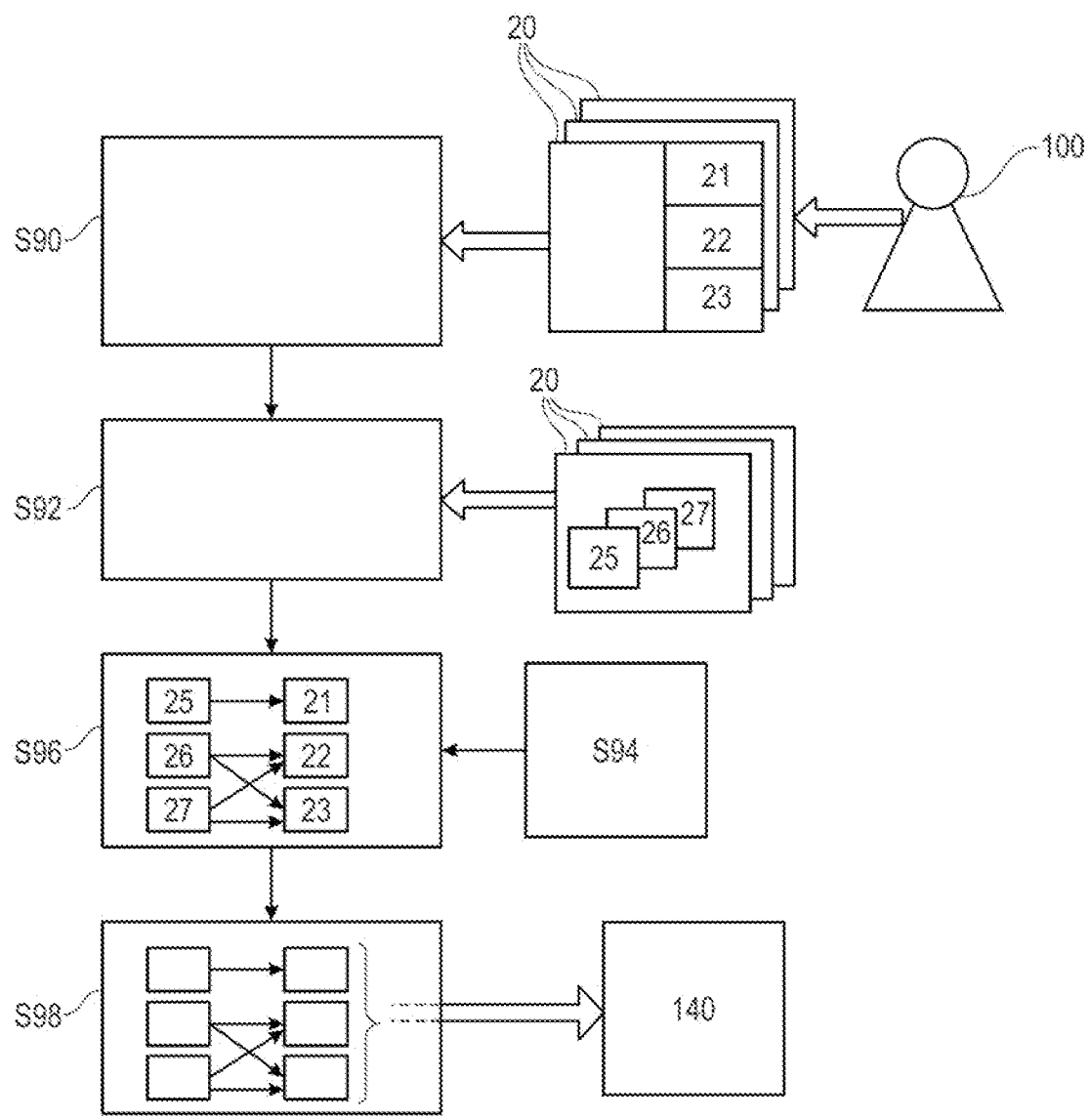
FIG. 5 shows a schematic sequence of a method of establishing a data basis for a method of monitoring and evaluating a production of a functional material in one embodiment of the invention.

FIG. 5 shows a schematic sequence of a method of establishing a data basis for a method of monitoring and evaluating a production of a functional material in one embodiment of the invention. This involves recording steps 21, 22, 23 taken by users in an implementation of a process 20 for production of a functional material S90. The properties 25, 26, 27 of the functional material produced by the process 20 for producing a functional material are analysed S92, and the properties 25, 26, 27 of the functional material produced by the process 20 for producing a functional material are assigned S96 to the corresponding steps 21, 22, 23 in an implementation of the process 24 producing a functional material. The assignment can be effected in a linear manner, as shown in FIG. 5 by way of example between the property 25 and the parameter 21, or else in a correlated manner, such as between the results 26 and 27 on the one hand and the parameters 22 and 23 on the other hand. The results of the assignment are then stored S98 in the data basis 140. The assignment can be effected on the basis of earlier processes 20, but also on the basis of correlations brought about analytically between the process parameters 21, 22, 23 and the properties 25, 26, 27 of the corresponding functional material. The assignment can also be effected on the basis of employment of artificial intelligence, in which, for example, correlations are recognized by means of a neural network and hence an assignment is effected.

Figure 6:
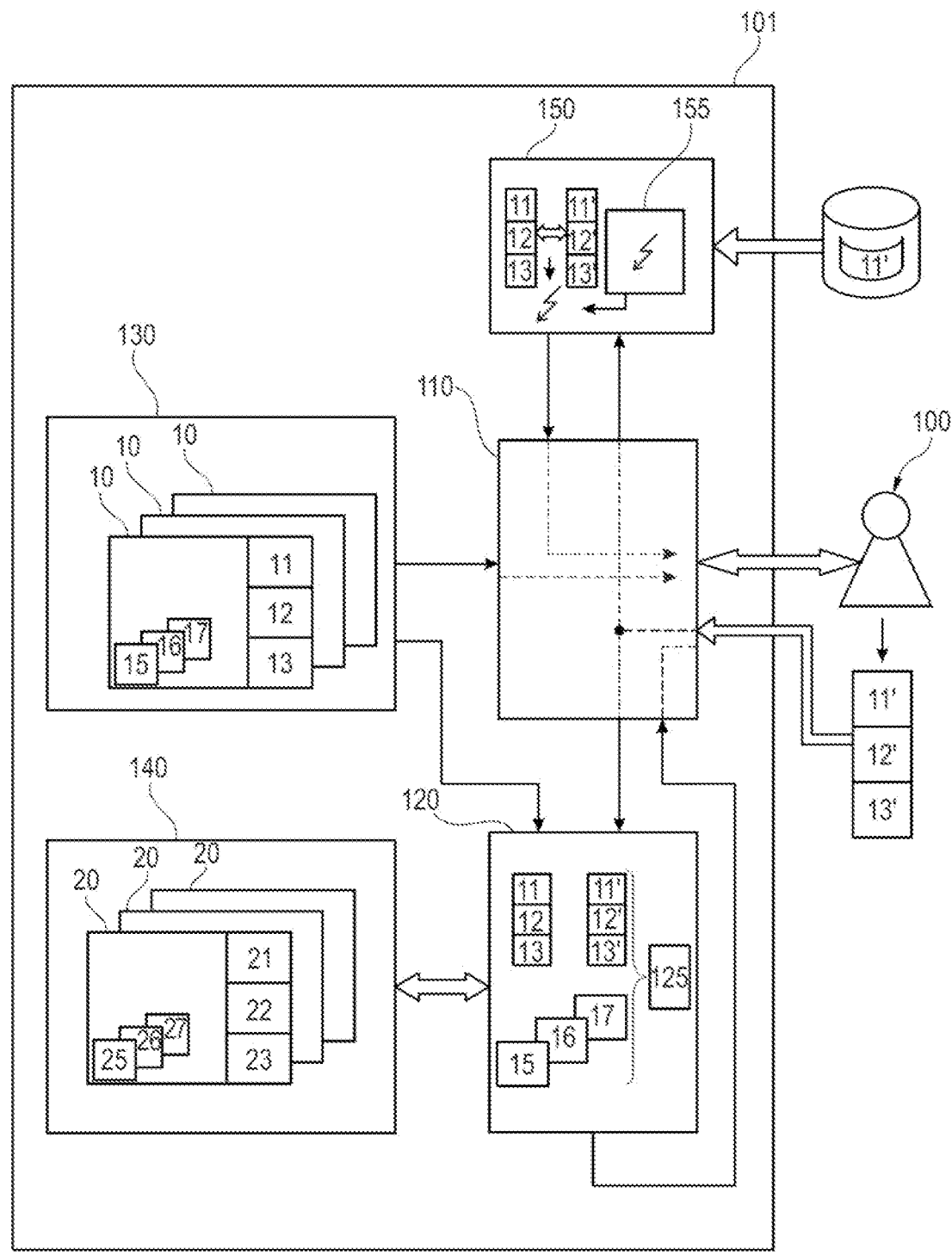
FIG. 6 shows the structure of an apparatus for monitoring and evaluating a production of a functional material in one embodiment of the invention.

FIG. 6 shows the structure of an apparatus for monitoring and evaluating a production of a functional material in one embodiment of the invention. The apparatus has a user interface 110 via which the user can communicate with the apparatus and via which the apparatus can give information to the user. The user interface 110 provides the user 100 with the catalog 130 comprising the processes 10 or the menus for selection of process parameters for the production of a functional material. The user interface 110 can also record steps 11', 12', 13' taken by the user in implementing a process 10 selected from the multitude of processes. In addition, a processing unit 120 is provided. The processing unit 120 may be set up to compare the steps 11', 12', 13' taken by the user with the process parameters 11, 12, 13 of a selected process 10 for the production of a functional material and to assess the steps 11', 12', 13' taken by the user based on the data basis 140 with regard to properties expected to be achieved in the functional material. The operation can be configured iteratively, such that the user can be constantly offered assistance. The processing unit 120 receives the appropriate information with regard to the selection by the user 100 from the catalogue 130 and the selection by the user and the actions of the user, especially the steps executed by the user, from the user interface 110. The processing unit 120 is connected to the data basis 140, in which a multitude of processes 20 implemented by earlier users for the production of functional materials and the analyzed properties thereof 25, 26, 27 are stored. The processing unit 120 compares the steps 11', 12', 13' taken by the user with the process parameters 11, 12, 13 of a selected process 10 for the production of a functional material and assesses the steps 11', 12', 13' taken by the user based on the data basis 140 with regard to properties expected to be achieved in the functional material. The user interface 110 is set up to report to the user the extent to which predetermined properties 15, 16, 17 of the functional material produced by the implemented process 10 are attained in the event of variances of the steps 11', 12', 13' taken in an implementation of the process selected from the defined process parameters 11, 12, 13 of the selected process 10. In addition, the apparatus includes a monitoring device 150 which compares a step 11', 12', 13' intended by the user 100 with an appropriate process parameter 11, 12, 13 of a selected process 10 for the production of a functional material, and gives a warning in the event of an impermissible variance. For this purpose, the monitoring unit 150 may have a reader unit 155 capable of reading an identifier 11' on a material vessel, which in this case constitutes a user step in order thus to record a material-based process parameter and to supply it to the comparison with the corresponding process parameter 11 of the process 10. The processing unit 120 may comprise artificial intelligence 125 set up, on the basis of the multitude of processes 20 executed by earlier users stored in the data basis 140, to establish a correlation of at least one process parameter 21, 22, 23 of a process 20 for the production of a functional material and at least one property 25, 26; 27 of the functional material. The artificial intelligence 125 can also be applied to the recorded parameters 11'; 12'; 13'; in order thus to predict the properties 15, 16, 17, it is possible here on the basis of a correlation and the steps it, 12', 13' taken by the user in an implementation of the selected process 10, to create a prediction is created for at least one property 15, 16, 17 of the functional material to be produced.

The method of the invention for monitoring and evaluating a production of a functional material can be implemented by a client-server architecture with a central database for data storage and interrogation. The client may be a Windows application which is started on the user's computer and connects to the server. Users can store so-called "synthesis requests" in a two-level order hierarchy of what are called projects and studies. These synthesis requests contain multiple constituents, for example: general information about synthesis request, for example project leader, contacts, desired completion date; materials that are required for the preparation; and/or a formulation editor. More particularly, for planning, there is a tab/menu in which the user is able to click on the process properties and/or instructions in a chart.

An intermediate sample can be taken at any process step, which is described analogously to a result sample. This may be of interest if performance of an analysis is desired for the intermediate sample. For the calculation of the target amount, it is possible to stipulate for each input material whether the entire material or individual/multiple components contribute to the target amount. In addition, an input material may also not contribute at all to the target amount.

Since it is frequently desirable in high-throughput research to produce multiple samples in a similar manner with variation of particular factors, several instances of a workflow can be stored. Each workflow instance can generate a separate result sample. In addition, it is possible to introduce factors that permit variation of amounts, materials or ratio factors. The description of the results sample can also be depicted via factors. Parameters of process steps can also be varied via a factor. The level for the factors can be input directly in the overview table of the workflow instances.

The linking of the target amount of a workflow instance allows exactly as much of the results sample to be produced as is used as input material overall in the subsequent workflow instances.

The preparation can be implemented simultaneously for one or more instances of a workflow. There are three main tasks during the execution: input of the weights of the starting materials, input of the actual parameter of the process steps, and input of the weights and storage locations of the result samples. Each workflow instance has a status and can first be started and then ended. The sequence has high flexibility, with regard to change in the process sequences. Interruptions or a termination of the performance of the sequence are possible here when, for example, input materials are out of stock or a change in prioritization is made, which leads to termination of sequence. When a workflow instance is started, the current state is copied from the formulation editor for this workflow instance. Subsequent amendments to the formulation have no effect on a started workflow instance. But a started workflow instance can be edited if the user notices that the original plan is not working. For example, input materials may not be present in the desired amount, it is necessary to use an input material from another manufacturer, or process steps have to be added or removed that were not foreseeable beforehand. A modal window is opened in a user interface, the function of which resembles the formulation editor. Changes can be adopted with a click on "Complete". The weight of the input materials can be entered in a table for multiple started and marked workflow instances. This involves recording barcodes in the weighing, and the actual weights. If the barcode does not correspond to the one planned, there is a warning. The difference between target and actual weight is displayed. The system is connected to a system for chemical inventory, in which registration on receipt, material in stock and withdrawal data are recorded, which the method accesses in the sequence. In the performance of the method, there is withdrawal of the materials that are detected by the method in the data basis. The user can thus be informed as to the requirements of reorders. If a material is not required for a particular workflow instance, the corresponding cell in the table is grayed out. The actual values for the parameters of the process steps can also be input in a table view that can be grouped according to various columns by drag & drop. The standard method is to group by process step and the index of the workflow instance. In a further tab/menu, it is possible to input information about the weight of the sample by input of tared and gross weight; or to directly input the actual amount, or about the storage location. Each storage location may be registered centrally in the system, and these can be managed on a separate administration page by users having appropriate access rights. In addition, it is also possible to undertake an automatic inventory of the feedstocks, such that, for example, for a sample A present in an amount of 550 g, 100 g is weighed out for a preparation, the amount of sample A is automatically updated to 450 g.

Each synthesis request has a status. The options here are as follows: request synthesis, where the synthesis request in this status can be assessed by a laboratory worker; start synthesis, after the synthesis has been requested—only then is it possible to start individual workflow instances in the execution; and conclude synthesis after all workflow instances have ended—it is thus considered to be fully implemented.

For the laboratory worker implementing the synthesis requests, an overview may be provided in the system, in which all synthesis requests can be filtered and sorted according to status and further criteria. The overview may also be searched with a free text search. Every individual synthesis request can be opened by a double-click. Unopened synthesis requests can be shown in bold type. In creating samples, the following information can be stored: the relation of the results sample to the starting materials used; sequence and names of the process steps; target and actual values of the parameters of the process steps including names and units; weights of the input materials including the unit; and an amount including the unit and storage location of the result samples.

Samples may be searched for by many features in the database. These may be related by logical linkages. Based on such a sample search, it is possible, for example, to display the abovementioned stored information.

LIST OF REFERENCE DESIGNATIONS 10 process, catalog process
11 process parameter, catalog process parameter
12 process parameter, catalog process parameter
13 process parameter, catalog process parameter
11' process step by a user
12' process step by a user
13' process step by a user
15 property of a (catalog) process product
16 property of a (catalog) process product
17 property of a (catalog) process product
20 process by an earlier user (learning process)
21 process parameter from a learning process
22 process parameter from a learning process
23 process parameter from a learning process
25 property of a product of a learning process
26 property of a product of a learning process
27 property of a product of a learning process
100 user
101 apparatus for monitoring/evaluating a production of a catalyst
110 user interface
120 processing unit
125 artificial intelligence unit
130 process catalog
140 data basis
150 monitoring unit
155 reading unit
S10 providing processes/a process catalog
S20 recording user steps
S30 assisting a user
S31 calculating ratios
S32 converting parameters
S40 monitoring a user
S42 comparing step intended by the user with process parameter
S43 warning to user
S45 reading an identifier of a reservoir vessel
S46 comparing identifier with process parameter/material
S47 warning to user
S50 comparing user steps with process parameters
S60 assessing the steps taken by the user
S61 intermediate assessment
S62 intermediate assessment
S65 applying artificial intelligence to assessment process
S70 reporting to the user
S90 recording process steps/parameters from earlier users
S92 analyzing properties of the earlier process results/catalysts
S94 applying artificial intelligence to establishment of the data basis
S96 assigning properties of a process result to process parameters
S96 storing the assignment results in data basis

The invention claimed is:

1. A method of monitoring and evaluating a production of a functional material, wherein the functional material is a catalyst, a battery material or an adsorbent, and wherein the method comprises:
providing a multitude of defined processes to a user, each with defined process parameters of a process for the production of a functional material and properties thereof,
recording steps taken by the user in implementing a process selected from the multitude of processes,
comparing the steps taken by the user with the process parameters of the selected process for the production of a functional material,
assessing the steps taken by the user based on a data basis having a multitude of processes implemented by earlier users with process parameters for the production of functional materials and the analyzed properties thereof,
reporting to the user the extent to which predetermined properties of the functional material produced by the implemented process are attained in the event of variances of the aforementioned steps in an implementation of the process selected from the defined process parameters of the selected process.

2. The method according to claim 1, wherein the method further comprises assistance for a user in a projection calculation, wherein the assistance especially comprises calculating of relationships and/or recalculating of parameters, wherein, in particular, at least some of the processes are scalable and a user is given the choice of dimensions of these processes.

3. The method according to claim 1, wherein the method further encompasses monitoring a user in implementing the steps made in a process selected from the multitude of processes.

4. The method according to claim 3, wherein the monitoring comprises comparing at least one step intended by the user with an appropriate process parameter of a selected process for the production of a functional material, and a warning in the event of an impermissible variance.

5. The method according to claim 3, wherein the monitoring comprises reading of an identifier of a reservoir vessel of a material provided by a user and a comparison with a material provided for the corresponding defined process, and a warning in the event of an impermissible variance.

6. The method according to claim 1, wherein a process parameter or a step taken by the user comprises at least one material parameter or one processing parameter, and/or an origin parameter of a material.

7. The method according to claim 1, wherein the assessing of the steps taken by the user comprises employing of artificial intelligence which, on the basis of the multitude of processes executed by earlier users stored in the data basis for the production of functional materials and the measured properties thereof, establishes a correlation of at least one process parameter of a process for the production of a functional material and at least one property of the functional material.

8. The method according to claim 7, wherein, on the basis of the correlation and the steps taken by the user in an implementation of the selected process, a prediction is created for at least one property of the functional material to be produced.

9. The method according to claim 1, wherein the assessing of the steps taken by the user comprises an intermediate assessment on the basis of an intermediate result based on a data basis comprising a multitude of processes implemented by earlier users for the production of precursor materials and the measured properties thereof.

10. A method of establishing a data basis for employment of a method according to claim 1, wherein the method comprises:
  recording steps taken by users in an implementation of a process for production of a functional material,
  analyzing properties of the functional material produced by the process for producing a functional material,
  assigning the properties of the functional material produced by the process for producing a functional material to the corresponding steps in an implementation of the process for producing a functional material,
  storing the result of the assignment in the data basis.

11. The method according to claim 10, wherein the method of establishing a data basis comprises employing of artificial intelligence which, on the basis of the multitude of recordings of steps taken by users in an implementation of a process for producing a functional material and the analyzed properties thereof, establishes a correlation of at least one process parameter of a process for the production of a functional material and at least one property of the analyzed functional material.

12. An apparatus for monitoring and evaluating a production of a functional material, wherein the functional material is a catalyst, a battery material or an adsorbent, and wherein the apparatus comprises:
  a user interface,
  a processing unit,
  a catalog having a multitude of defined processes, each with defined process parameters of a process for the production of a functional material, and
  a data basis having a multitude of processes implemented by earlier users for the production of functional materials and the analyzed properties thereof,
  wherein the user interface is set up to provide the user with the catalog for selection, and to enable the user to select a process for the production of a functional material,
  wherein the user interface is set up to record steps taken by the user in implementing a process selected from the multitude of processes,
  wherein the processing unit is set up to compare the steps taken by the user with the process parameters of a selected process for the production of a functional material and to assess the steps taken by the user based on the data basis with regard to properties expected to be achieved in the functional material,
  wherein the user interface is set up to report to the user the extent to which predetermined properties of the functional material produced by the implemented process are attained in the event of variances of the aforementioned steps in an implementation of the process selected from the defined process parameters of the selected process.

13. The apparatus according to claim 12, wherein the apparatus includes a monitoring device set up to compare at least one step intended by the user with an appropriate process parameter of a selected process for the production of a functional material, and to give a warning to the user in the event of an impermissible variance.

14. The apparatus according to claim 12, wherein the processing unit comprises artificial intelligence set up, on the basis of the multitude of processes executed by earlier users stored in the data basis for the production of functional materials and the measured properties thereof, establishes a correlation of at least one process parameter of a process for the production of a functional material and at least one property of the functional material.

15. The apparatus according to claim 14, wherein, on the basis of the correlation and the steps taken by the user in an implementation of the selected process, a prediction is created for at least one property of the functional material to be produced.

* * * * *